United States Patent [19]

Lee et al.

[11] Patent Number: 4,722,889

[45] Date of Patent: Feb. 2, 1988

[54] IMMUNOASSAYS USING MULTIPLE MONOCLONAL ANTIBODIES AND SCAVENGER ANTIBODIES

[75] Inventors: Jin P. Lee, Troy; F. Brad Salcedo, Ann Arbor; Martin F. Robins, Troy, all of Mich.

[73] Assignee: Leeco Diagnostics, Inc., Southfield, Mich.

[21] Appl. No.: 718,921

[22] Filed: Apr. 2, 1985

[51] Int. Cl.$^4$ .............. G01N 33/543; G01N 33/577; G01N 33/76

[52] U.S. Cl. .................................. 435/7; 435/28; 435/188; 435/810; 436/518; 436/531; 436/532; 436/533; 436/534; 436/539; 436/540; 436/548; 935/110

[58] Field of Search .............. 435/7, 28, 810, 188; 436/518, 531–534, 548; 935/110

[56] References Cited

U.S. PATENT DOCUMENTS

| | | | |
|---|---|---|---|
| 4,161,519 | 7/1979 | Talwar | 436/541 |
| 4,376,110 | 3/1983 | David | 435/7 |
| 4,467,031 | 8/1984 | Gallati | 435/7 |
| 4,508,643 | 4/1985 | Calaorari | 436/547 |
| 4,514,505 | 4/1985 | Canfield | 435/7 |
| 4,565,687 | 1/1986 | Khazaeli | 435/7 |

FOREIGN PATENT DOCUMENTS

| | | | |
|---|---|---|---|
| 0158973 | 10/1985 | European Pat. Off. | 435/7 |
| 0201853 | 12/1982 | Japan | 435/7 |
| 0054966 | 3/1984 | Japan | 435/4 |
| 85/00663 | 2/1985 | PCT Int'l Appl. | 435/7 |

OTHER PUBLICATIONS

Hoofnagle, Gastroenterology, 72, pp. 290–296, 1977.

Primary Examiner—Sidney Marantz
Assistant Examiner—Robert Benson
Attorney, Agent, or Firm—Krass & Young

[57] ABSTRACT

A method and reagent kit means are provided for assay of a selected antigen such as hCG or CEA in an aliquot of body fluid. The method comprises the steps of constituting the aliquot in a mixture comprising tracer (which may be an enzyme tracer or a radioactive tracer) conjugated with monoclonal antibody, and separate immobilized monoclonal antibody, incubating the mixture to enable separation of a solid phase antigen antibody conjugate in sandwich relation, and measuring the tracer content and corresponding antigen content of the aqueous phase or the solid phase. The antibody (conjugated and/or immobilized) comprises multiple monoclonal antibodies from different cell lines so that the specificity of the assay is enhanced, and the possibility of unrecognized antigen fragments is reduced. Also, as a preferred option, the incubation may be carried out with a scavenger monoclonal antibody so that, as an example, in the context of hCG assay, the scavenger chosen for beta subunit selectivity but low hCG affinity is present in the reaction to prevent any possible cross reactivity from analogs of homologous reactivity.

7 Claims, No Drawings

IMMUNOASSAYS USING MULTIPLE MONOCLONAL ANTIBODIES AND SCAVENGER ANTIBODIES

DESCRIPTION

This invention relates broadly to a new in vitro assay method and reagent kit means for determining the presence and concentration of a selected antigen or analyte in body fluid, such as human chorionic gonadotropin (hCG), carcinoembryonic antigen (CEA) and the like.

BACKGROUND OF THE INVENTION

Human chorionic gonadotropin is normally present in serum of males and non-pregnant females at concentrations below 10 mIU/ml. Structurally, hCG is a glycopeptide hormone (M.W.-40,000) consisting of two distinct amino acid chain subunits, designated as alpha and beta. Following conception, the concentration produced by the placenta during pregnancy in serum and urine alike increases steadily to a peak of as much as 100,000-200,000 mIU/ml at the 7th to 12th week. This increased level in the maternal system prevents normal involution of the corpus luteum and in the male fetus stimulates steroid production by the testes. Elevations of hCG are also found in trophoblastic neoplasms such as hydatidiform mole and choriocarcinoma.

Recently, the highly sensitive techniques of radioimmunoassay and enzymeimmunoassay have been applied to the analysis of hCG. Earlier radiometric assays utilized the intact biologically active hCG molecule as the antigen source for development of a binding entity. Since the pituitary hormones, thyroid stimulating hormone (TSH), follicle stimulating hormone (FSH) and luteinizing hormone (LH) also contain alpha subunits closely related to that of the hCG, the antibodies or membrane receptors for intact hCG produce non-specific binding and cross reaction with these hormones.

Chemically, CEA is a glycoprotein with a molecular weight of approximately 200,000 daltons that is secreted into the glycocalyx of gastrointestinal cells of the 2-6 month old human fetus. It was first presented as a specific antigen for adenocarcinoma of the colon. More recent studies however, have demonstrated CEA in a variety of malignancies and particularly those involving ectodermal tissue of gastrointestinal or pulmonary origin.

This multiplicity of antigen expression as well as the existence of potentially cross reacting compounds has limited the diagnostic value of many potential tumor markers. The prognostic utility of CEA when employed as a monitoring device has however been well established for several types of carcinoma. In general, a persistently elevated CEA finding following treatment is indicative of continuing disease whereas a decreasing value represents a favorable response to therapy.

Originally, radioimmunoassay has served as the basis for most determinations of CEA. Recently, sensitive and procedurally less complicated enzymeimmunoassays for carcinoembryonic antigen have been introduced.

However, the art lacks simple, rapid and reliable means for the immunoassay of antigens and analytes.

It is therefore an object of the present invention to provide improved means for assaying the content of antigen (compound, protein, or ligand) in a body fluid sample.

It is also an object of the invention to provide a new enzyme immunoassay (EIA) using multiple monoclonal antibodies having polyvalent reactivity in sandwich relation with a selected antigen or analyte.

It is another object of the invention to provide a new immunoradiometric assay (IRMA) using multiple monoclonal antibodies having polyvalent reactivity in sandwich relation with a selected antigen or analyte and yet having the advantage of polyclonal antibodies (See *Nature*, 296, 200-202, 1982).

A further object of the invention is to provide broadly applicable means for immunoassay of any of various exogenous or endogenous antigens, compounds, haptens or ligands.

These and other objects, features and advantages of the present invention will become apparent from the following description.

SUMMARY AND DETAILED DESCRIPTION

In one aspect, the invention concerns a storage-stable reagent kit for assay of a selected antigen in body fluid. The reagent kit of the invention comprises as a first component, tracer conjugate with monoclonal antibody and as a second component, monoclonal antibody immobilized by solid support means. The monoclonal antibody of both components is immunospecific for the selected antigen, and at least one of the components comprises two or more separate genetically different monoclonal antibodies each having monovalent specificity for the selected antigen. The components are constituted such that, when subjected to liquid phase incubation with an aliquot containing a significant quantity of the selected antigen, the first and second components become mutually bound at immunospecific binding sites with the selected antigen in sandwich relation comprising multiple monovalent binding. This enables separation of the tracer bound selected antigen in solid form, free of non-specific antigen and unbound enzyme, and detection by tracer assay means. A preferred tracer for purposes of the invention is an enzyme tracer such as horseradish peroxidase or a radioactive tracer either of which may be a conventional tracer.

In one preferred embodiment for assay of hCG, the reagent kit contains antibodies immobilized in a test tube. For this purpose, dual monoclonal antibodies with divalent hCG reactivity and very rapid kinetics characteristics are bonded to the inside surface of a polystyrene test tube. This minimizes the incubation times necessary for high sensitivity. Another two immunologically different monoclonal antibodies with C-terminal beta subunit reactivity and high affinity are conjugated to a suitable tracer (e.g., enzyme or radioactive tracer) and lyophilized in the antibody coated tube. In a preferred embodiment, still another antibody, a "scavenger" antibody, is present in the reaction. The scavenger antibody may be polyclonal but preferably is monoclonal. The scavenger antibody is characterized by beta subunit selectivity and both low affinity for hCG and high affinity for cross reactant hCG analogs such as LH, FSH, and TSH. The scavenger antibody is present in the reaction in sufficient amount to scavenge the cross reactants and prevent unwanted cross reactivity. In the test, with or without scavenger, hCG from a patient sample attaches to the antibodies on the tube surface and is thus bound to the solid support. Simultaneously, the patient sample reacts with the antibody-tracer conjugate to complete the sandwich mechanism. The resultant Solid-Ab-hCG-Ab-Tracer structure is then washed to remove unattached tracer and the bound tracer is measured. Where the bound tracer is an enzyme, a chromophore substrate is added and the subsequent color reaction observed spectrophotometrically. Where the bound tracer is radioactive, the activity is read radiometrically.

In another preferred embodiment for assay of CEA, the assay kit contains antibody immobilized on a plastic bead. For this purpose, monoclonal antibody with rapid kinetics characteristics is coated to a polystyrene bead. This minimizes the incubation time necessary for high sensitivity. In a test container (assay well) endogenous CEA from the patient sample attaches to this antibody and is thus bound to the solid support. A conjugate of a tracer (e.g., an enzyme or radioactive tracer) and dual monoclonal antibodies with distinct antigen selectivity and high CEA affinity are added to the reaction. By utilizing antibodies from different cell lines with distinct selectivity, the specificity of the assay is enhanced and the possibility of unrecognized antigen fragments is reduced. The resultant Solid-Ab-CEA-Ab-Tracer structure is then washed to remove unattached tracer and the amount of bound tracer is measured. Thus for an enzyme tracer, a substrate is added and the subsequent color reaction observed spectrophotometrically. For a radiotracer, the activity is read radiometrically. The response is then compared to that of a set of standard CEA solutions for quantitation of the patient carcinoembryonic antigen. The monoclonal antibodies from different cell lines used in the components of the reagent kit are available commercially or are made by conventional means (*Journal of Immunological Methods*, 39, 285–308, 1980) and are immobilized or conjugated, as required, by conventional means (U.S. Pat. No. 4,376,110).

The invention is applicable for measuring any of a wide variety of antigens, compounds, analytes, haptens and ligands which are measurable by conventional immunoassay methods. For example, the invention is particularly suited to the assay of hCG and CEA and other analytes such as TSH—thyroid stimulating hormone, LH—luteinizing hormone, FSH—follicle stimulating hormone, PRL—prolactin, AFP—alpha feto protein, PAP—prostatic acid phosphatase, and other large molecular weight multi-determinant antigens. The invention is applicable to body fluids in general and to blood plasma, serum, spinal fluid and urine in particular. The substance assayed will, for convenience be sometimes referred to herein as an antigen, but it will be understood that this term is used generically to include or define other endogenous and exogenous analyte substances as well. Also, for purposes of illustration, the invention is described at length with reference to assay of hCG and CEA, but it will be understood that the invention in art-recognized ways, is applicable broadly to antigens.

In another aspect, the invention concerns a method for assay of a selected antigen in an aliquot of body fluid employing a reagent kit using multiple monoclonal antibodies having polyvalent reactivity in sandwich relation with the selected antigen, as described herein, which comprises constituting the aliquot in an aqueous mixture with components of the reagent kit, incubating the mixture to enable separation of the antibody bound antigen conjugate as a solid phase, and isolating and measuring the tracer content in at least one of the aqueous or solid phases.

The invention is illustrated and the best mode of carrying out the same is described in the following examples.

EXAMPLE 1

Assay Method for Carcinoembryonic Antigen (CEA)

Materials and Reagents

1. Antibody Coated Beads . . . One bottle containing 100 polystyrene beads coated with mouse monoclonal anti-carcinoembryonic antigen antibody. Store at 2°–8° C.

2. Enzyme Conjugate . . . One bottle (20 ml) containing a dual mouse anti CEA monoclonal antibody-horseradish peroxidase conjugate in 0.1M Tris buffer and 0.01% Thimerosal. Store at 2°–8° C.

3. Dilution Buffer . . . One bottle (30 ml) containing 0.15M NaCl, 1.0% BGG, 0.01% Tween 20 and 0.01% Thimerosal; The solution is color coded red. Store at 2°–8° C.

4. CEA Standards . . . Four bottles (2.0 ml each) containing 4.0, 10, 30 and 60 ng/ml and one bottle (5 ml) of 0.0 ng/ml of carcinoembryonic antigen in Tris Buffer with protein stabilizer and 0.01% Thimerosal. Store at 2°–8° C.

5. Substrate Tablets . . . One bottle containing 10 tablets (24 mg each) of orthophenylenediamine—2 HCl. Store at 2°–8° C.

6. Substrate Buffer . . . One bottle (60 ml) containing a citric acid-phosphate buffer and 0.02% hydrogen peroxide and 0.01% Thimerosal. Store at 2°–8° C.

7. CEA Controls . . . Two bottles (2.0 ml each) containing a normal (Level I) and elevated (Level II) concentration of carcinoembryonic antigen in a human serum base and 0.1% sodium Azide. Store at 2°–8° C.

8. Sulfuric Acid . . . One bottle (110 ml) of 1.0N $H_2SO_4$. Store at 2°–25° C.

Specimen Collection

Sample:

Serum (0.5 ml)—No additives or preservatives are necessary to maintain the integrity of the specimen, however, plasma from sequestrantized (EDTA) blood may be employed in lieu of serum. Grossly hemolyzed samples should not be used.

Sample:

Store refrigerated (2°–8° C.) unless analysis will be delayed beyond 24 hours, then store frozen (−20° C.); avoid repeated freezing and thawing. Thawed aliquots should be mixed thoroughly before analysis.

Procedure Instructions

Label duplicate assay wells on the bead trays and reaction tube racks for all patients, standards and control serums.

1. Pipette 0.1 ml of patients, standards and control serums to the appropriate well.

2. Add 0.1 ml of Dilution buffer to each well and mix gently by tapping the sides of the tray.

3. Add one (1) Antibody Coated Bead to each well and mix gently by tapping the sides of the tray.

4. Incubate each tray for 1 hour at 45° C.

5. Remove the seal from the bead trays and wash each bead at least three times with at least 4.0 ml of distilled water each rinse.

6. Add 0.2 ml of Enzyme Conjugate solution onto each bead, mix gently and reseal the trays with a new cover seal.

7. Incubate each tray for 1 hour at 45° C.

8. During the second incubation, prepare a working Substrate reagent by adding of one Substrate Tablet to 5 ml. of Substrate Diluent.

9. Remove the seal from the bead trays, wash the beads thoroughly at least three times with at least 4.0 ml of distilled water each rinse.

10. Flip-transfer each bead to the appropriately labeled Reaction tube.

11. Add 0.3 ml of Substrate reagent to each tube, vortex mix gently and incubate at room temperature for 15 minutes.

12. Add 1.0 ml of 1N $H_2SO_4$ to all tubes; vortex mix thoroughly and determine the absorbance of all tubes against distilled water.

FLOW CHART

| SAMPLE | SERUM or PLASMA | DILUTION BUFFER | | | ENZYME CONJUGATE | | | WORKING SUBSTRATE | 1 N $H_2SO_4$ |
|---|---|---|---|---|---|---|---|---|---|
| 0, 4, 10, 30, 60 ng/ml standards | 0.1 ml | 0.1 ml | Mix & incubate at 45° C. for 1 hour | Wash three times with $H_2O$ | 0.2 ml | Mix & incubate at 45° C. for 1 hour | Wash 3 times with $H_2O$ | 0.3 ml | 1.0 ml |
| Level I | 0.1 ml | 0.1 ml | | | 0.2 ml | | | 0.3 ml | 1.0 ml |
| Level II | 0.1 ml | 0.1 ml | | | 0.2 ml | | | 0.3 ml | 1.0 ml |
| Patient Sample | 0.1 ml | 0.1 ml | | | 0.2 ml | | | 0.3 ml | 1.0 ml |

Calculation of Results

1. Determine the optical density of each standard, control and patient sample at 492 nm against a distilled water blank.

2. Construct a standard curve by plotting the mean optical density of each standard against its concentration on rectilinear graph paper.

3. Determine the value of patient and control samples by reference to the curve.

Sample Data

| Tube | Sample | Average O.D. | ng/ml |
|---|---|---|---|
| 1,2 | 0.0 ng/ml | .081 | |
| 3,4 | 4.0 ng/ml | .162 | |
| 5,6 | 10.0 ng/ml | .266 | |
| 7,8 | 30 ng/ml | .621 | |
| 9,10 | 60 ng/ml | 1.239 | |
| 11,12 | Level I | .164 | 2.2 |
| 13,14 | Level II | .448 | 19.5 |
| 15,16 | Patient #1 | .271 | 10.0 |

Example: Patient serum

Average net optical density of patient—0.271

By interpolation the O.D. of 0.271 is found to yield 10.0 ng/ml of CEA.

Performance Characteristics

Accuracy:

To assess the accuracy of the system, a recovery study was conducted by spiking a low patient pool with increasing amounts of a high concentration of human CEA stock.

| Added CEA ng/ml | Observed Value ng/ml | Expected Value ng/ml | % Recovery |
|---|---|---|---|
| Patient Base — | 2.2 | — | — |
| 0.8 | 3.2 | 3.0 | 106.7 |
| 1.6 | 3.8 | 3.8 | 100.0 |
| 3.2 | 5.9 | 5.4 | 109.3 |
| 6.4 | 9.3 | 8.6 | 108.1 |
| 12.7 | 14.7 | 14.9 | 98.7 |

Precision:

| | Pool #1 | Pool #2 | Pool #3 |
|---|---|---|---|
| Intra Assay (n = 11) | | | |
| Mean (ng/ml) | 2.7 | 11.2 | 23.1 |
| S.D. (ng/ml) | 1.05 | 0.21 | 0.57 |
| C.V. (%) | 1.7 | 1.9 | 2.5 |
| Inter Assay (n = 13) | | | |
| Mean (ng/ml) | 2.8 | 11.3 | 23.3 |
| S.D. (ng/ml) | 0.10 | 0.48 | 0.86 |
| C.V. (%) | 3.5 | 4.2 | 3.7 |

Specificity:

The assay system was conducted on patient samples in the presence of excessive hemolysis, bilirubin and lipemia. No interference was noted up to the concentrations indicated.

| Bilirubin | 30.0 mg/dl |
|---|---|
| Hemoglobin | 8.0 g/dl |
| Total lipids | 1700 mg/dl |
| Triglycerides | 700 mg/dl |

Sensitivity:

A linearity study was performed to assess the sensitivity of the procedure by a serial dilution of a high concentration stock solution with the zero base.

| Dilution (v/v) Stock | Observed (ng/ml) | Expected (ng/ml) |
|---|---|---|
| 1:1 | 40 | — |
| 1:2 | 20 | 20 |
| 1:4 | 10.6 | 10.0 |
| 1:8 | 5.4 | 5.0 |
| 1:16 | 2.8 | 2.5 |

The sensitivity by this study was <0.1–0.6 over the entire range.

A minimum detectable dose as calculated by determining two standard deviations of 20 replicates of the zero standard was found to be 0.2 ng/dl.

EXAMPLE 2

Assay Method for Human Chorionic Gonadotropin (hCG)

Materials and Reagents

1. Reaction Tubes—25 (12×75) clear test tubes containing coated dual monoclonal mouse antibodies (IgG) directed against hCG and lyophilized dual monoclonal mouse IgG antibodies (against hCG) conjugated to horseradish peroxidase and 0.02% Thimerosal. Store at 2°–8° C. In a preferred option, the dual antibody enzyme conjugate is in liquid form (0.1M Tris buffer and Thimerosal) and is provided in a supply container separate from the immobilized antibody.

2. Substrate Chromogen—One bottle (3.0 ml) containing 1.8 mg of substrate chromogen in 0.1N HCl. Store at 2°–8° C.

3. Substrate Diluet—One bottle (10.0 ml) containing 0.02% hydrogen peroxide in 0.065M Acetate buffer and 0.02% Thimerosal. Store at 2°–8° C.

4. Reference Tube—One 12×75 mm clear test tube containing FD&C blue #1 dye adjusted to represent the color intensity of 50 mIU/ml of hCG. Store at 2°–8° C.

5. Calibrated Droppers—25 plastic capillary tubes and two (2) rubber bulbs for sample delivery.

Specimen Collection

Sample:

Urine (0.5 ml)—The sample must be collected in a clean, dry container without preservative. Specimens collected at any time may be used, however, the first morning urine generally contains the highest concentration of hormone. Cellular and crystalline elements should first be removed by centrifugation or filtration prior to analysis.

Serum (0.5 ml)—No additives or perservatives are needed to maintain the integrity of the specimen, however, plasma from sequestrantized (EDTA) blood may be employed in lieu of serum.

STORAGE:

Store refrigerated (2°–8° C.) unless analysis will be delayed beyond 48 hours, then store frozen (−20° C.); avoid repeated freezing and thawing. Thawed aliquots should be mixed thoroughly before analysis.

Procedure Instructions

1. Add 0.2 ml of patient sample (serum or urine) and 0.2 ml of positive, negative or reference sample if desired into an appropriately labeled reaction tube.

2. Mix gently by shaking the test tube rack to thoroughly dissolve the lyophilized material and allow the tube to stand undisturbed for 10 minutes at room temperature.

3. Decant the entire contents of the tube and "wash" a minimum of four times by:
  (a) filling the tube at least ¾ full with distilled water
  (b) decanting all liquid from the tube
  (c) blotting the rim of the tube onto absorbent paper to remove all water following the final wash.

4. Add one (1) drop (0.05 ml) of substrate chromogen from the small dropper bottle and five (5) drops (0.3 ml) of substrate diluent from the large dropper bottle directly onto the tube.

5. Mix gently by shaking the test tube rack and allow to stand undisturbed at room temperature for 10 minutes.

6. Compare the intensity of the blue color in the patient tube to that of the 50 mIU/ml reference. A deeper blue color in the patient tube is a positive reaction. A colorless or blue color of equal or less intensity than the 50 mIU/ml reference should be considered as a negative finding.

Expected Values

Serum hCG levels during pregnancy are estimated to be:

10–30 mIU/ml—16–23 days from LMP
30–100 mIU/ml—24–30 days from LMP
100–1000 mIU/ml—31–38 days from LMP Therefore, the assay will yield a positive result on the average sometime between the 7th and 14th day post conception.

Precision

Intra Assay

Within run precision was determined using 20 replicates of five specimens containing 0, 10, 30, 80 and 100 mIU/ml of hCG. The negative, borderline and positive values were correctly identified 100% of the time.

Inter Assay

Between run precision was determined using the same five specimens of 0–100 mIU/ml of hCG in 20 independent assays, with 3 different lots of reagents over a 30 day period. Again, the negative, borderline positive findings were correct 100% of the time.

Specificity

The following substances were tested in specimens both positive and negative for hCG and were found to have no effect on the results up to the listed concentration:

| | |
|---|---|
| acetaminophen | 200 mcg/ml |
| ascorbic acid | 1000 mcg/ml |
| gentisic acid | 200 mcg/ml |
| phenothiazine | 200 mcg/ml |
| acetyl salicylic acid | 200 mcg/ml |
| atropine | 200 mcg/ml |
| methadone | 200 mcg/ml |
| caffeine | 200 mcg/ml |
| hLH | 550 mIU/ml |
| hFSH | 1000 mIU/ml |
| hTSH | 1000 mIU/ml |

Sensitivity

The protocol detects human chorionic gonadotropin concentrations in either serum or urine below 50 mIU/ml as indicated by patient samples yielding a blue color reaction less intense than that of the Reference Tube or Positive Serum or Urine Reference. The cut off level of 50 mIU/ml was selected because hCG concentrations of 50 mIU/ml are usually achieved the 2nd week post conception.

EXAMPLE 3

Data Showing the Effect of a Scavenger Antibody on the Degree of LH Cross Reactivity on an EIA and IRMA βhCG Assay For an assessment of the effect of scavenger antibody on luteinizing hormone (LH) cross reactivity, the procedure of Example 2 is followed for assay of beta-hCG in separate runs using enzyme tracer or radiotracer ($^{125}$I), with and without scavenger monoclonal antibody with beta subunit selectivity but low hCG affinity. The results are as follows:

EIA

| No Scavenger | | Scavenger | |
| --- | --- | --- | --- |
| Sample | Absorbance | Sample | Absorbance |
| 0 mIU/ml | .013 | 0 mIU/ml | .012 |
| 6 | .066 | 6 | .041 |
| 25 | .222 | 25 | .126 |
| 50 | .456 | 50 | .236 |
| 200 | 1.738 | 200 | .910 |
| LH(500) | .076 | LH(500) | .025 |
| PMF | .031 | PMF | .021 |

LH(500) = serum pool containing 500 mIU/ml of luteinizing hormone; PMF = post menopausal female serum pool The LH pool when run as an unknown for βhCG in the absence of the scavenger antibody showed 6 mIU/ml interference. In the presence of the scavenger antibody, the cross reactivity was reduced well below 6 mIU/ml. The PMF sample showed a similar but slightly less pronounced decrease in the cross reactivity between the two assays.

IRMA

| No Scavenger | | Scavenger | |
| --- | --- | --- | --- |
| Sample | CPM | Sample | CPM |
| 0 mIU/ml | 294 | 0 mIU/ml | 300 |
| 5 | 2739 | 5 | 2185 |
| 10 | 5130 | 10 | 4149 |
| 20 | 9507 | 20 | 7215 |
| 40 | 17399 | 40 | 13500 |
| 80 | 33015 | 80 | 26180 |
| 160 | 62593 | 160 | 46052 |
| LH(1000) | 24377 | LH(1000) | 4521 |

FSH(1000), TSH(1000), LH(1000) = serum pools containing 1000 mIU/ml of follicle stimulating hormone, thyroid stimulating hormone and luteinizing hormone respectively.

The LH pool when run as an unknown for βhCG gave >40 mIU/ml while in the presence of the scavenger antibody the cross reactivity dropped to approximately 10 mIU/ml.

What is desired to claim as our exclusive property in the invention, as described, is the following:

1. A storage-stable reagent kit for immunoassay of the antigen human chorionic gonadotropin (hCG) in an aliquot of body fluid, hCG having two distinct amino acid chain subunits designated as alpha and beta, comprising:
   a. as a first component, tracer conjugated to monoclonal antibody and
   b. as a second component, monoclonal antibody immobilized by solid support means, the monoclonal antibody of both components being immunospecific for the hCG antigen such that each antibody reacts with a different epitope of the antigen and at least one of the components has two or more monoclonal antibodies for the hCG antigen;
   and a further component that is a scavenger antibody characterized by beta subunit selectivity and both low affinity for the hCG antigen and high affinity for the cross reactant analogs luteinizing hormone (LH), follicle stimulating hormone (FSH), and thyroid stimulating hormone (TSH), the scavenger antibody being present in an amount sufficient to prevent unwanted reactivity between the monoclonal antibodies of said first component and said second component with the said cross reactant analogs of the hCG antigen, the components being constituted such that, when subjected to liquid phase incubation with an aliquot containing the hCG antigen, the cross reactant analogs are scavenged and the first and second components become mutually bound at immunospecific binding sites with the hCG antigen in sandwich relation thereby preventing said cross reactivity and enabling separation of the tracer bound hCG antigen in solid form free of non-specific antigen and unbound tracer and detection by tracer assay means.

2. A reagent kit according to claim 1 where the solid support means is a test tube support means.

3. A reagent kit according to claim 2 where the first component is contained in the test tube support means and is in stable lyophilized form or liquid form.

4. A reagent kit according to claim 1 where the tracer conjugate is a conjugate with the enzyme horseradish peroxidase.

5. A reagent kit according to claim 1 where the monoclonal antibody is mouse antibody.

6. A method of assay of hCG antigen in an aliquot of body fluid employing a reagent kit according to claim 1 which comprises constituting the aliquot in an aqueous mixture with components of the reagent kit, incubating the mixture to allow separation of the said hCG antigen in solid form, separating the aqueous phase and the solid phase, and measuring the tracer content in at least one of the aqueous and solid phases.

7. A sensitive, rapid, and accurate immunometric assay for the antigen hCG in a sample of body fluid, hCG having two distinct amino acid chain subunits designated as alpha and beta, which assay comprises:
   (a) contacting the sample with dual labeled monoclonal antibodies specific to the antigen to form a soluble labeled complex of the antibodies and antigen;
   (b) contacting the sample with at least one unlabeled soluble scavenger monoclonal antibody characterized by beta subunit selectivity and both low affinity for hCG and high affinity for cross reactive substances LH, FSH and TSH to prevent the formation of a complex between the labeled antibody and the cross reactive substances which are present in said sample;
   (c) contacting the soluble complex with other dual monoclonal antibodies which are specific to the antigen sufficient to form an insoluble complex with the labeled antibody-antigenic complex, the said other dual monoclonal antibodies being bound to a solid carrier;
   (d) separating said solid carrier from the fluid sample and unreacted labeled antibody; and
   (e) determining the presence of or measuring labeled antibody associated with solid carrier or unreacted labeled antibody associated with the fluid sample.

* * * * *